United States Patent [19]
Ball et al.

[11] Patent Number: 4,976,686
[45] Date of Patent: Dec. 11, 1990

[54] IMPLANT GUN

[75] Inventors: Keith V. Ball, Burwood; Karl-Heinz Halblander, Hampton Park; Barry N. Loftus, Collingwood, all of Australia

[73] Assignee: Schering Agrochemicals Limited, Hauxton, England

[21] Appl. No.: 246,344

[22] Filed: Sep. 19, 1988

[30] Foreign Application Priority Data

Sep. 18, 1987 [AU] Australia ............................ PI4456
Jan. 19, 1988 [AU] Australia ............................ PI6354

[51] Int. Cl.⁵ .......................................... A61M 31/00
[52] U.S. Cl. ........................................ 604/61; 604/62; 606/117
[58] Field of Search .............................. 604/57, 59–63, 604/57–64; 128/330; 124/45; 606/116, 117

[56] References Cited

U.S. PATENT DOCUMENTS

| | | | |
|---|---|---|---|
| 797,183 | 8/1905 | Davis | 604/63 |
| 1,347,622 | 7/1920 | Deininger | 604/61 |
| 3,153,500 | 10/1964 | Pachmayr . | |
| 3,428,169 | 2/1969 | Hilti . | |
| 3,693,220 | 9/1972 | Pabich et al. . | |
| 3,774,607 | 11/1973 | Schmitz | 604/61 |
| 3,812,961 | 6/1979 | Merrick et al. . | |
| 4,077,406 | 3/1978 | Sandhage et al. | 604/62 |
| 4,106,618 | 8/1978 | Haytayan . | |
| 4,154,239 | 5/1979 | Turley | 604/61 |
| 4,447,223 | 5/1984 | Kaye et al. | 604/61 |
| 4,451,254 | 5/1984 | Dinius et al. . | |
| 4,474,572 | 10/1984 | McNaughton et al. | 604/61 |
| 4,531,938 | 2/1985 | Kaye et al. . | |
| 4,560,061 | 12/1985 | Haytayan . | |
| 4,574,954 | 3/1986 | Reid . | |
| 4,576,591 | 3/1986 | Kaye et al. | 604/61 |
| 4,720,374 | 1/1988 | Ramachandran . | |
| 4,762,515 | 8/1988 | Grimm | 604/61 |

FOREIGN PATENT DOCUMENTS

0090899 10/1983 European Pat. Off. .
840276 7/1960 United Kingdom .
1583816 2/1981 United Kingdom .

Primary Examiner—Stephen C. Pellegrino
Assistant Examiner—Ralph Lewis
Attorney, Agent, or Firm—Randall A. Hillson

[57] ABSTRACT

An implant gun for implanting an insert or pellet into or below tissue of an animal. The gun has a body comprising a barrel, a hand grip and a trigger mounted on the hand grip for successive manual firing operations. At least a portion of the barrel defines a guideway along which a series of pellets are movable to present each, in turn, to a discharge position from which it can be discharged from the gun. The body houses discharge and advance mechanisms, with the discharge mechanism being operable by manual operation of the trigger in a firing operation, to discharge from the barrel a pellet presented to the discharge position and the advance mechanism being operable to index the series of pellets along the guideway.

27 Claims, 11 Drawing Sheets

IMPLANT GUN

This invention relates to an improved gun for implanting an insert or pellet into or below tissue of an animal, such as skin or muscle tissue.

Many forms of drugs, vitamins, and trace elements and like materials can be implanted into or below animal tissue for a variety of purposes. In some instances, the material can be provided in the form of a pellet and implanted to achieve sustained release over a useful period. Typically such pellets are implanted by means of an implant gun having a hollow needle through which a pellet is ejected after inserting the needle into or below tissue of the animal, such as into slack skin tissue behind an animals ear.

Prior implant guns have suffered from a number of disadvantages. One such disadvantage is their low level of reliability in terms of their mechanical operation. A further disadvantage arises from uncertainty as to a successful firing operation and, hence, whether a pellet has been implanted into a given animal on completion of that operation.

An implant gun according to the present invention has a body comprising a barrel, a hand grip and a trigger mounted on the hand grip for successive manual firing operations; at least a portion of the barrel defining a guideway along which a series a pellets are movable to present each, in turn, to a discharge position from which it can be discharged from the gun; the body housing discharge and advance mechanisms, with the discharge mechanism being operable by manual operation of the trigger in a firing operation, to discharge from the barrel a pellet presented to the discharge position and the advance mechanism being operable to index the series of pellets along the guideway.

The pellets for use with the gun may be held in a cartridge of strip form. Each pellet preferably is located in a respective one of a series of pockets formed in, and spaced along, the cartridge. The cartridge may be of a construction enabling it to be indexed longitudinally along the guideway, by operation of the advance mechanism on completion of actuation of the discharge mechanism, to present a successive one of the pellets to the discharge position on completion of each firing operation.

The gun is intended to be hand held and preferably is similar in overall size and configuration to a conventional hand gun. However, it is not intended to discharge pellets as projectiles. Rather, the gun is intended to implant a pellet into or below skin or muscle tissue of an animal. Accordingly, the gun preferably has a hollow needle mounted at the outlet of the barrel; the needle being insertable into the skin or muscle tissue to enable a pellet to be discharged into or below the tissue.

In one form, the discharge mechanism includes an elongate ejection pin which extends longitudinally within the barrel. The ejection pin is longitudinally movable such that, during each firing operation, the pin is moved from a retracted position in which a forward end thereof is located rearwardly with respect to an outlet of the barrel, to an advanced position in which the forward end of the pin projects through the outlet sufficiently to eject a pellet previously presented to the discharge position. On completion of a firing operation, the ejection pin is returned to its retracted position. Such return most preferably is under the action of resilient biasing means, such as a coil spring, with the ejection pin being movable to its advances position against the action of the biasing means.

Particularly where such ejection pin is provided, the discharge position for successive pellets most preferably is located closely adjacent and in line with the forward end of that pin and the outlet of the barrel. While other arrangements are possible, the guideway preferably extends forwardly along the barrel, such as along the top of the barrel, and has a terminal portion of arcuate form which curves across the outlet of the barrel. In such arrangement, the series of pellets, preferably in a cartridge of strip form, is indexed along the barrel, and then in a curved path extending across the outlet, to present successive pellets to the discharge position in line with the outlet. While a major portion of the length of the guideway may be on the exterior of the barrel, its terminal portion preferably is within the interior of the barrel such as to extend across the outlet rearwardly of the latter.

The ejection pin may be movable between its positions under the action of a slide member movable between corresponding retracted and advanced positions. The pin may be integral with or connected to the slide member. In forms in which the pin is returned to its retracted position under the action of biasing means, this preferably is by the biasing means acting on the slide member. The slide member preferably is movable along a track, channel or guideway defined within the barrel, such as by longitudinal ribs formed on the inner surface of opposed sides of the barrel.

In one form, the slide member is in the form of a straight toothed bar member movable linearly within the barrel under the action of a gear wheel engaged therewith and mounted within the barrel for rotation on a fixed axis. In such form, the gear wheel preferably is rotatable in a first direction, in which it moves the slide member and the ejection pin to their advanced positions, under the action of the trigger, upon the latter being squeezed from a rest position for a firing operation. The trigger most preferably is urged to the rest position by a return spring, with the latter providing a resilient force against which the trigger is squeezed in a firing operation.

Where the slide member is a toothed bar movable under the action of a rotatable gear wheel meshing therewith, rotation of the gear wheel is translated into linear movement of the bar. In such arrangement, squeezing of the trigger preferably gives rise to substantially linear motion of a drive portion of the trigger, or of an actuating member movable by the trigger. This substantially linear motion is translated to rotational motion of the gear wheel in the first direction by means of a driving connection between the trigger and the gear wheel. In order to provide a required extent of rotation of the gear wheel and, hence, a sufficient linear movement of the bar member from its retracted to its advanced position, the trigger preferably is pivoted on a pivot pin remote from the barrel, such as adjacent the remote or lower end of the hand grip, with an end of the trigger adjacent the barrel being reversably movable by pivoting of the trigger on that pivot pin.

Drive from the trigger to the gear wheel may be provided by a number of arrangements. Thus, the end of the trigger adjacent the barrel, or an actuating member movable with the trigger as the latter is squeezed during a firing operation, may have a linear or arcuate series of teeth engaged directly or indirectly with the gear wheel to cause rotation of gear wheel as the trigger is squeezed. The series of teeth on the trigger or actuating member may engage the gear wheel on the side thereof diametrically opposed to that side engaged by the slide member; the series of teeth preferably being moved rearwardly with respect to the barrel to rotate the gear wheel in the first direction and causing forward movement of the slide member. Most preferably, the drive from the trigger to the gear wheel is operational only during squeezing of the trigger, and is disengaged when the trigger is squeezed to complete a firing operation. Such disengagement of the drive enables reversal of the direction of rotation of the gear wheel under the action of biasing means acting on the slide member and independent return of the trigger to its rest position.

Where the series of teeth are on an actuating member movable with the trigger, the actuating member preferably is a straight toothed bar. In that form, the actuating member may be movable endwise along a track, channel or guideway defined within the body of the gun adjacent the junction of the barrel and hand grip. The actuating member may have an abutment face or shoulder at which a force is applied on squeezing the trigger, with the force acting to move the actuating member. The trigger preferably has a portion which abuts the face or shoulder such that, on squeezing the trigger, the actuating member is pushed along such track, channel or guideway. That portion may be moved clear of the face or shoulder when the trigger is fully squeezed to complete a firing operation. The trigger may be pivotally mounted such that its portion which engages the face or shoulder moves through an arcuate path which, when the trigger is fully squeezed, carries that portion away from the line of movement of the actuating member and, hence, out of engagement with the face or shoulder. Alternatively, engagement between the trigger and the face or shoulder may be by means of a catch member pivotally mounted on the trigger; with the catch member being constrained, by pivoting in one direction relative to the trigger, to remain in contact with the face or surface until the trigger has been fully squeezed. Such catch member preferably is resiliently urged in the one direction by biasing means, such as a spring, with a guide or camming member preferably causing pivioting of the catch member in the reverse direction, out of contact with the face or surface, when the trigger has been fully squeezed.

While the trigger, or actuating member moveable therewith, may directly engage and drive the gear wheel, indirect drive is possible. Thus, the drive may be to at least one secondary gear in driving engagement with the gear wheel. Particularly in such indirect drive arrangement, a drive ratio can be chosen which results in movement of the slide member, from its retracted to its advanced position, which exceeds the distance moved by the trigger in a firing operation.

The advance mechanism is positioned so as to engage the series of pellets, such as by means of a strip cartridge in which the pellets are held. The advance mechanism preferably is operable to advance the series, on completion of a firing operation to eject one pellet, so as to position the next pellet of the series at the discharge position. The advance mechanism may include at least one index wheel which engages the series of pellets. Such wheel may be rotatable for advancing the series and is rotated in a step-wise fashion through a small arc on completion of each firing operation.

Where the pellets are spaced along a strip cartridge, the cartridge may have longitudinally spaced formations which are engaged by complementary formations spaced circumferentially around the index wheel. In one arrangement, the cartridge may have formations comprising lateral tabs, with the wheel having circumferentially spaced protrusions or ribs between which the tabs locate to enable the series of pellets to be indexed by the wheel. A respective series of tabs may extend to each side of the cartridge, with a respective index wheel being provided at each side of the guideway for the series of pellets.

Where the guideway for the series of pellets has a portion of arcuate form, such as detailed above, the or each index wheel preferably is rotatable on an axis within the arc, such as substantially co-incident with the centre of curvature of that portion. The or each index wheel may be rotatable on a hub member mounted within the barrel. A common hub member preferably is provided where there are two index wheels, with the wheels being axially spaced on that hub. With such common hub, a transverse opening may be formed therein, between the two wheels, with the ejection pin extending through the opening at least when in its advanced position.

In one form, the advance mechanism is actuated in response to actuation of the discharge mechanism, on completion of a firing operation. Where the discharge mechanism has a slide member as detailed above, the or each index wheel may be rotatably indexed by an indexing member adjustably engaged with the or each index wheel and reversably movable for advancing the latter. The or each index wheel may be a ratchet wheel, with the indexing member having a toothed finger engaged with a tooth of the ratchet wheel. In such arrangement, the indexing member may be caused to index the wheel, such as by the slide member contacting and retracting the indexing member during a final stage of movement of the slide member in returning to its retracted position. Similarly, the slide member, in a final stage of its movement to its advanced position, may contact and advance the indexing member to enable its finger to engage the next tooth on the ratchet wheel. Preferably the finger of the indexing member is resilient to enable it to the flex and pass a tooth of the ratchet wheel, by which it previously indexed the latter, to enable it to engage the next tooth. The indexing member preferably is substantially linearly adjustable within barrel. It may, if required, be adjustable along a track, channel or guideway defined by the barrel. The indexing member preferably has a rearward and a forward abutment by which it is alternately contacted by the slide member.

In a first alternative form, the advance mechanism is as outlined in the immediately preceding paragraph, except that the indexing member is not advanced and retracted by means of the slide member, but by a coupling member provided between the trigger and the indexing member. As the trigger is squeezed in a firing operation, it advances the slide member, while it also retracts the slide member as it returns to its rest position. The coupling member may comprises a lever or toggle pivotally mounted intermediate its ends within the gun body, such as adjacent the junction of the barrel and hand grip, and having respective ends coupled to the trigger and the indexing member. The arrangement preferably is such that, as the trigger is squeezed during a firing operation, the end of the lever or toggle coupled to the trigger is drawn therewith and the lever or toggle is pivoted so as to move its other end in the opposite direction and thereby advance the indexing member.

With that arrangement, return of the trigger to its rest position causes reversal of the pivoting of the lever or toggle and thereby retracts the indexing member. A toothed finger of the indexing member preferably is operable to index the or each ratchet wheel, such as in the manner detailed in the preceeding paragraph, as the coupling member causes the slide member to be advanced and retracted by the trigger.

In a second alternative form, the advance mehanism is actuated independently of the trigger and actuation of the discharge mechanism. Again, the advance mechanism includes an indexing member which may be as described in the two immediately preceding paragraphs. However, coupled to the indexing member, there is a control member which is manually accessible for movement of the indexing member from one to the other of two extreme positions. The control member may be a supplementary trigger able to be squeezed from a rest position to retract the indexing member so that the latter indexes the indexing wheel. The indexing member preferably is biased towards an advanced position, such as by a spring acting on the indexing member or the supplemental trigger, the bias also causing the supplemental trigger to be returned to its rest position when released. The supplemental trigger may be located adjacent the trigger for actuating the discharge mechanism, such as between the latter trigger and the underside of the barrel.

In a variant of the second alternative form, the control member may simply comprise a control knob or the like which is accessible from the exterior of the gun body and movable along a guideway defined by that body. Manual movement of the knob from a rest position at one end of the guideway draws the indexing member so as to index the index wheel. Biasing means acting on the indexing member or the knob preferably acts to return the indexing member and knob to reposition these members for a next indexing operation.

In each arrangement of the second alternative form, the indexing member preferably has at least one toothed finger member by which it is opearable to index the or each indexing wheel. The arrangement of such finger may be as described above in relation to the first form of the advance mechanism.

In each form of the advance mechanism, there preferably is at least one detent member for resiliently engaging the or each indexing wheel, to ensuring indexing of the latter through only a single indexing position each time the advance mechanism is actuated. The or each detent member may comprise a resilient detent finger mounted in the barrel and resiliently engaging the periphery of its index wheel.

In order that the invention may more readily be understood, description now is directed to the accompanying drawings in which.

Figures 1, 3, 4, 6:
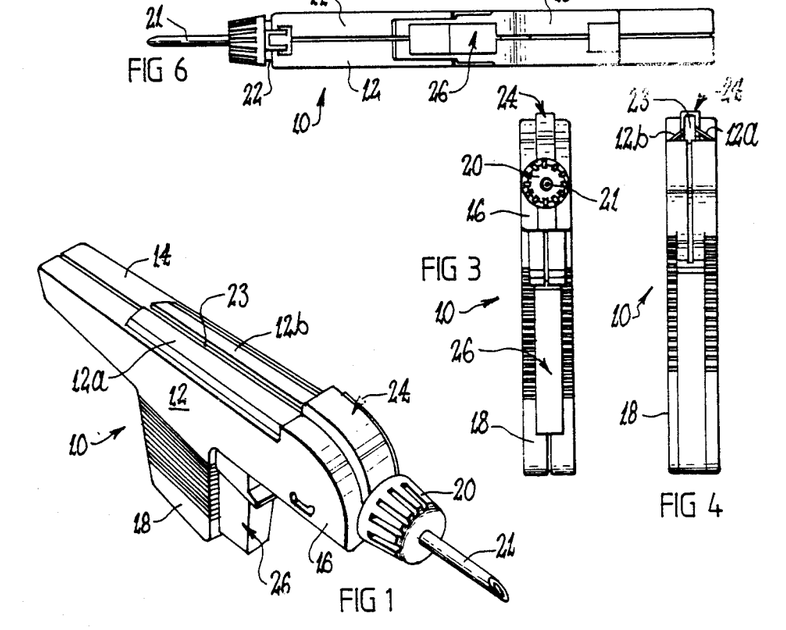
FIG. 1 is a front perspective view of a gun according to the invention.
FIGS. 3 to 6 show front and rear elevations and top and bottom plan views of the gun of FIG. 1.
Figures 2, 5:
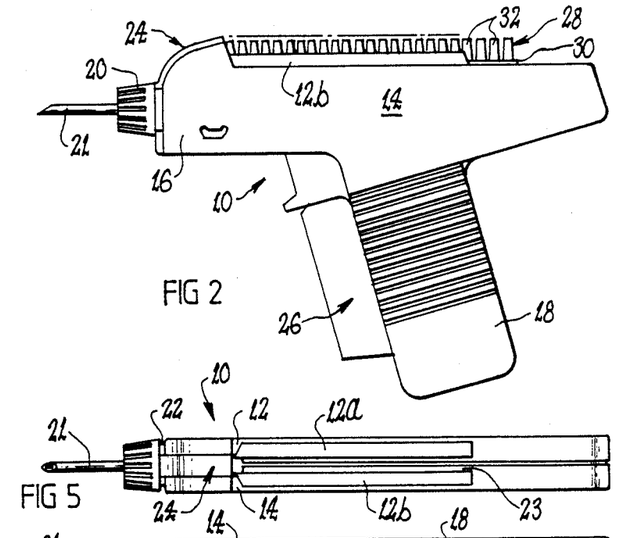
FIG. 2 is a side elevation of the gun according to FIG. 1.
Figure 7:
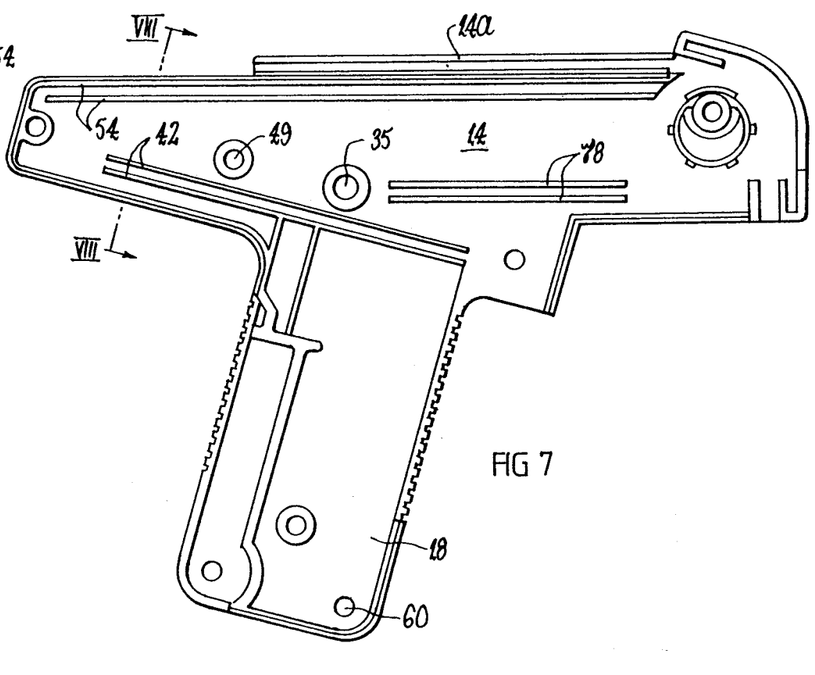
FIG. 7 is a sectional view of the left hand half of the casing of the body of the gun of FIG. 1 with separable components removed, the right hand half being of substantially complementary form.
Figure 8:
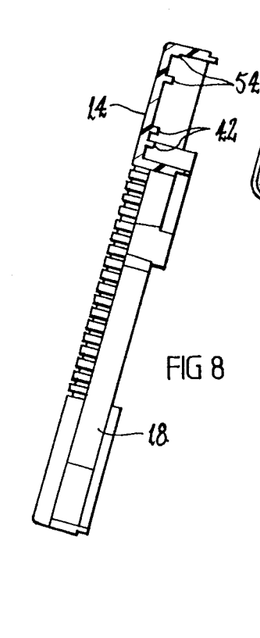
FIG. 8 is a view on line VII—VII of FIG. 7.

With reference to FIGS. 1 and 2, the gun 10 has a body having left and right hand half casings 12, 14 and defining a barrel 16 and a hand grip or handle 18. The body is hollow and has, at the outlet of barrel 16, a nut 20 screwed onto a hollow boss 22. Nut 20 is hollow, and retains a hollow, sharp-tipped needle 21 in line with the outlet of barrel 16.

Along the top of barrel 16, each casing 12, 14 has a flange 12a, 14a which curves upwardly and laterally toward the other casing. The adjacent edges of flanges 12a, 14a are spaced to define an open guideway 23 which is somewhat of an inverted T-form. Guideway 23 is continued internally within a feed guide 24 (see FIGS. 12 and 13) held between casings 12, 14 at the forward end of barrel 16. Within guide 24, a continuation of guideway 23 is of arcuate form, and extends downwardly across the outlet of barrel 16. Below barrel 16, guideway 23 terminates at an opening 25.

Figure 9:
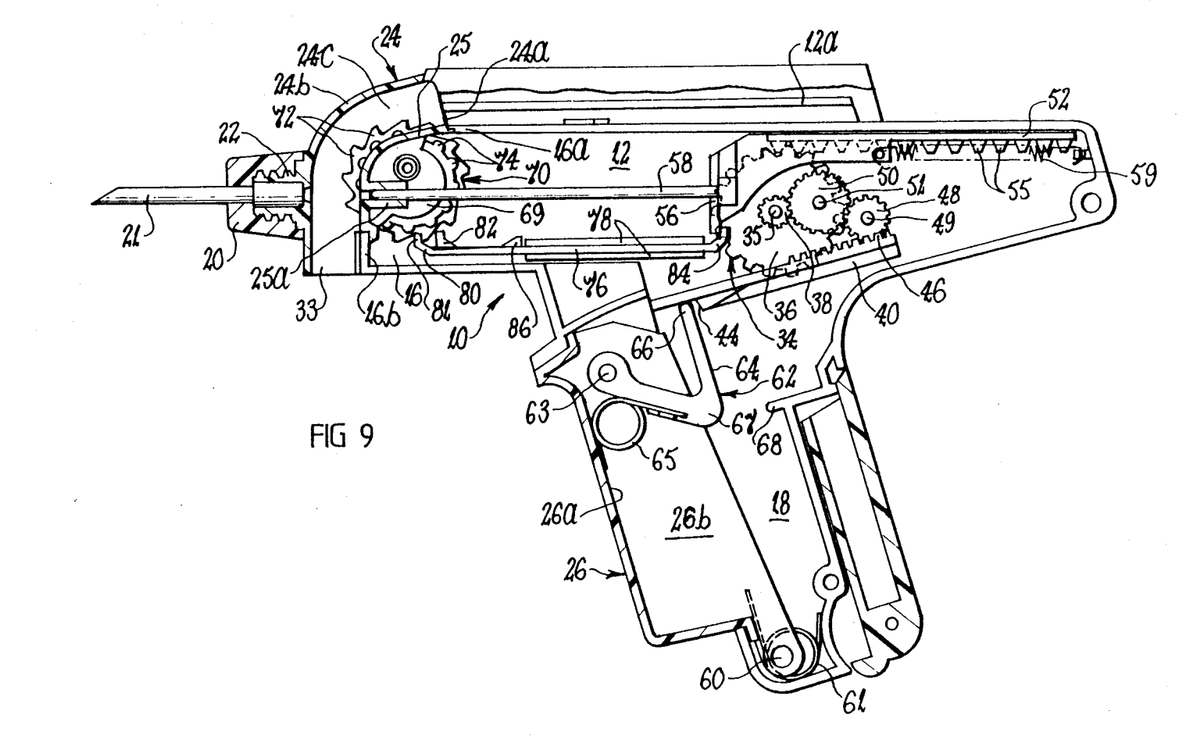
FIG. 9 shows detail of the gun of FIG. 1.
Figures 12, 13, 14, 15:
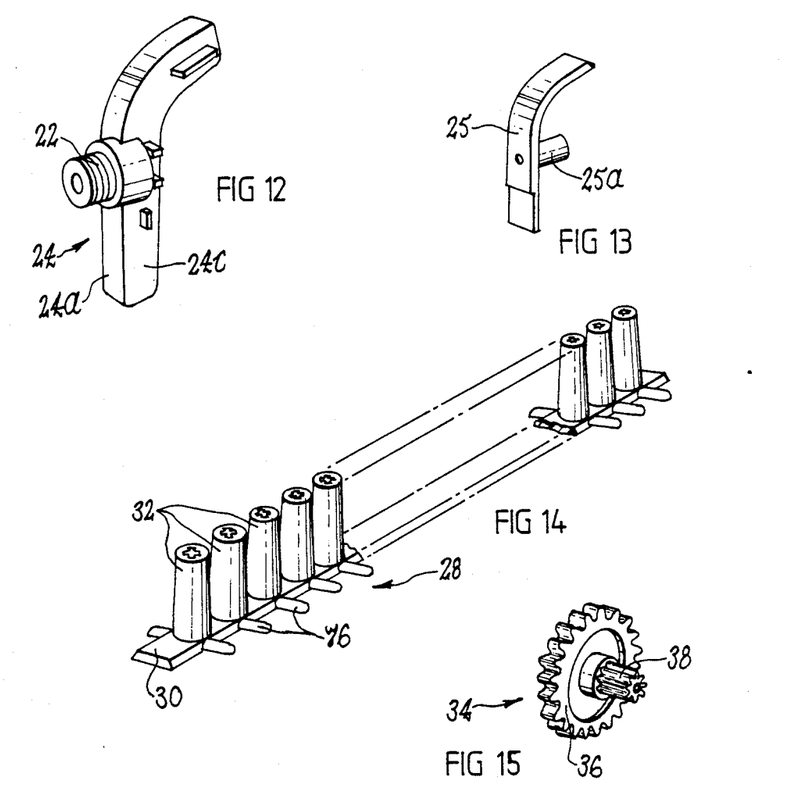
FIGS. 12 to 20 show components of the guns of FIGS. 1 to 9, 10 and 11.

As is apparent from FIGS. 9, 12 and 13, guide 24 has an arcuate body 24a with which boss 22 is integral. In transverse section, body 24a is of U-shape, as shown in FIG. 6, having a web 24b and side flanges 24c. Within the opening around the edges of flanges 24c remote from web 24b, guide 24 includes an arcuate member 25 having an integral sleeve 25a projecting away from body 24a in axial alignment with boss 22. The ends of member 26 are supported by top wall 16a and abutment 16b of barrel 16 to secure member 25 in position. Body 24a is retained between casings 12, 14. The width of member 25 laterally of barrel 16 is less than the spacing between flanges 24c, such that a respective arcuate gap exists between member 25 and each flange 24c.

Handle 18 has a trigger 26 by which integral mechanisms of the gun are actuated. However, before describing these mechanisms, a brief explanation of use of gun 10 will be described in broad outline.

As shown in FIG. 1, an elongate cartridge 28 is inserted along guideway 23, from the rear end thereof, so as to extend as far as it can be pushed into the continuation of the guideway within guide 24. As shown in FIG. 14, cartridge 28 has an elongate basal strip 30 along which there is a plurality of upstanding cylindrical pellet holders 32. The bore of each holder 32 opens through strip 30 and houses a pellet (or a plurality of pellets) of a composition required to be implanted into an animal. In end elevation, cartridge 28 has an inverted T-form, complementary to that of guideway 23, to enable cartridge 28 to move endwise along the guideway. With cartridge 28 positioned as indicated, trigger 26 is squeezed a number of times to perform successive firing operations. During each such operation, cartridge 28 is indexed forwardly by the distance between centers of successive holders 32, until the leading holder is at a discharge position in line with the outlet of barrel 16 and the bore of needle 21 and sleeve 25a; the curvature of the continuation of guideway 23 in guide 24 presenting successive holders 32 at the discharge position coaxially with respect to needle 21. On the next and subsequent firing operations, a respective pellet is ejected through needle 21, with cartridge 28 thereafter issuing from opening 33.

Figure 17:
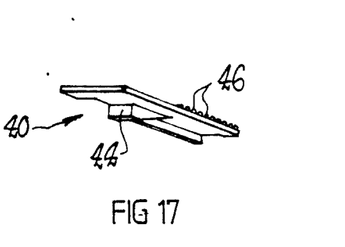

Within the body of gun 10, there is a gear member 34 mounted for rotation on transverse pins 35 which project inwardly from each casing 12, 14. As shown in FIG. 15, gear member 34 has a larger diameter spur gear 36, and a smaller diameter spur gear 38 concentric with gear 36. Below gear portion 38, there is an elongate actuating member 40 (see also FIG. 17) in the form of a toothed bar. Member 40 has one side thereof located between guide ribs 42 on casing 12 and, at each end thereof, a respective lateral tab 41 (see FIG. 17) engaged between similar ribs 42 on the other casing 14. Thus member 40 is slidable longitudinally of barrel 16. The underside of member 40 defines a forwardly facing shoulder 44 by which member 40 is engaged by trigger 26 so as to be rearwardly movable, along respective ribs 42 on squeezing trigger 26 in a firing operation.

Teeth 46 on the upper surface of member 40 mesh with a drive gear 48; the latter being rotatable on pins 49 on casing 12, 24 located rearwardly of gear member 34. A secondary gear 50 rotatable on pins 51 is meshed with gear 48 and with spur gear 38 such that movement of member 40 along ribs 42 rotates gear 48 and, via gear 50, causes rotation of gear member 34.

Figure 18:
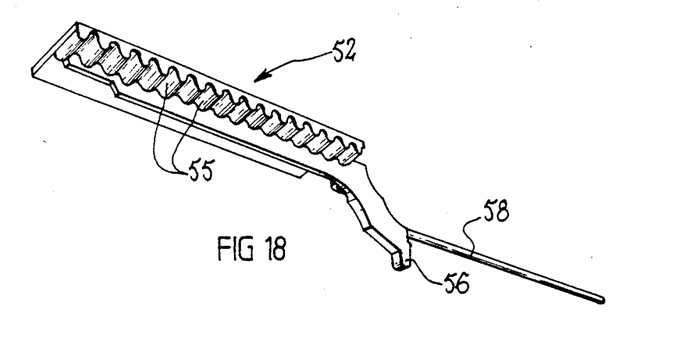

Above gear member 34, there is an elongate slide member 52 which also is shown in FIG. 18 and is in the form of a straight toothed strip. As with member 40, member 52 is longitudinally slidable by having its sides located between respective pairs of guide ribs 54 on each casing 12, 14. On its underside, teeth 55 of member 52 mesh with gear 36, such that on rotation of gear 36 as described, member 40 moves forwardly or rearwardly between retracted and advanced positions relative to barrel 16.

At its forward end, member 52 has a depending finger 56 from which an ejection pin 58 projects forwardly within barrel 16 and in line with the bore of sleeve 25a and needle 21. With member 52 in its retracted position, in which it abuts the rear of the body of gun 10, the forward end of pin 58 is located within sleeve 25a, but rearwardly of the discharge position for a pellet to be ejected. When member 52 is moved to its advanced position, pin 58 is advanced so that its forward end projects through sleeve 25a and slightly beyond the tip of needle 21. Thus, pin 58 is able to force a pellet at the discharge position out of its holder 32 and through needle 21, to cause the pellet to be ejected from the gun.

Such movement of pin 58 is effected by squeezing trigger 26, and resultant rearward movement of member 40, rotation of gears 48, 50 and gear member 34, and forward movement of member 52. At the stage when pin 58 has just protruded beyond needle 21, trigger 26 is disengaged from member 40, and trigger 26 is able to return to its rest position, in a manner hereinafter described. Upon such disengagement, member 52 is returned to its retracted position, drawing with it pin 58. The return of member 52 is effected by a coil spring 59 (shown in FIG. 9), connected between member 52 and the rear end of the body of gun 10; spring 59 providing a bias on member 52 urging it to its retracted position, and being tensioned on movement of member 52 to its advanced position. Also, the return of member 52 to its retracted position causes reversal of the rotation of member 34 and gears 50, 48, resultant forward movement of member 40 and return of trigger 26 to its rest position.

Trigger 26 is pivoted within handle 18 on pins 60 projecting from each casing 12, 14 at the base of handle 18. In horizontal section, trigger 26 is of U-section, with the web 26a of the U providing a forward, finger-engaging face thereof. A conventional return spring 61 is provided between flanges 26b of trigger 26 and acts on web 26a to bias the upper end of trigger 26 outwardly to its rest position. On squeezing trigger 26, its upper end moves rearwardly.

Figure 16:
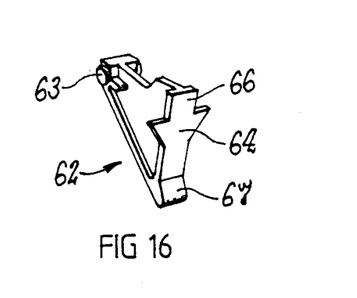

At the upper end of trigger 26, a triangular catch member 62 (see also FIG. 16) is pivotally mounted between flanges 26b of the trigger. Member 62 is mounted at one corner thereof by means of a pivot pin 63 extending between flanges 26b of trigger 26. The side 64 of member 62 remote from the one corner retained by pin 63 is located rearwardly of flanges 26b. A spring 65 acting between trigger 26 and member 62 biases the latter so that a second corner 66 thereof is urged into engagement with shoulder 44 of member 40, and it is by this means that member 40 is engaged by trigger 26.

As trigger 26 is squeezed, member 62 moves with it and spring 65 acting on member 62 retains corner 66 in contact with member 40 throughout the major distance through which trigger 26 is moved. However, before trigger 26 is fully squeezed, but on completion of a firing operation, the leading side 64 of member 62 adjacent the third corner 67 thereof hits abutment 68 of one casing. Abutment 68 causes pivoting of member 62 against the bias of spring 65, releasing the engagement of corner 66 from shoulder 44. As a consequence, member 52 which has been moved to its advanced position, is able to return to its retracted position under the action of the spring 59. In fact, spring 59 snaps member 52 back to its retracted position, causing member 52 to hit the rear of the body of gun 10, causing a positive noise indicative of a successful firing operation.

Figure 19:
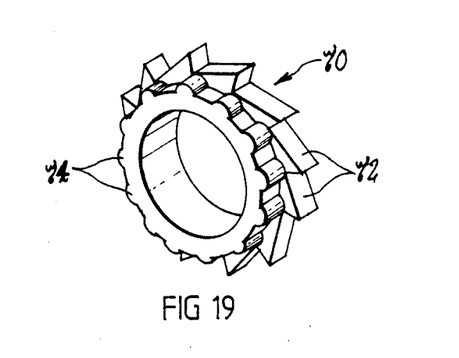

At the forward end of barrel 16, there is a hub member 69 which is non-rotatably mounted between casings 12,14. On each end of member 69, adjacent each of casings 12,14, there is a respective index wheel 70 of which one is shown in detail in FIG. 19 (the other being a mirror image). Each wheel 70 has peripheral ratchet teeth 72 and, inwardly of teeth 72, a plurality of transverse, circumferentially spaced ridges or ribs 74. The spacing and location of ribs 74 is such that they mesh with lateral tabs 76 spaced along cartridge 28. The arrangement is such that, as wheels 70 rotate, cartridge 28 is drawn around the continuation of guideway 23, within guide 24, so as to issue from opening 33.

An opening in hub 69, between wheels 70, enables pin 58 to extend therethrough and to advance and retract with member 52.

As detailed above, a respective arcuate gap exists between member 25 of guide 24 and each flange 24c of body 24a of guide 24. As shown in FIG. 9, for one of index wheels 70, part of the circumference of each of wheels 70 extends into guideway 70 through a respective one of those gaps. The guide ribs 78 of each wheel thus is able to engage cartridge 28 within guide 24 such that, as wheels 70 are indexed, cartridge 28 also is indexed along guideway 23 and through guide 24.

Figure 20:
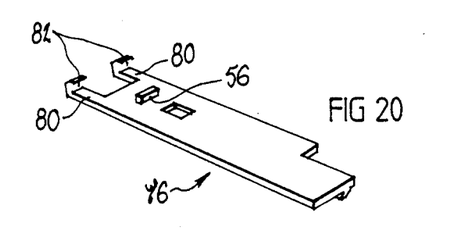

Extending between wheels 70 and gear member 34, there is located an elongate strip member 76 also shown in FIG. 20. Opposed sides of member 76 are located in guide ribs 78 of each casing 12,14 for limited movement along barrel 16. At the forward end of member 76, there is a respective forwardly extending resilient finger 80 terminating adjacent each wheel 70. Each finger 80 has a tooth 81 engaged with the teeth 72 of its wheel 70. Also, member 76 has an upstanding tab 82,84 at each of its forward and rearward ends, with finger 56 being located between and vertically overlapping with tabs 82,84.

As member 52 reaches its advanced position, finger 56 contacts tab 82 and moves member 76 forwardly, to locate each tooth 81 behind the next tooth 72 of each wheel. As member 52 reaches its retracted position, finger 56 contacts tab 84, pulling member 76 rearwardly with resultant rotation of wheels 70 through one index position. As a consequence cartridge 28 is advanced by the spacing between centers of holders 32, to present at the discharge position a pellet to be ejected on the next firing operation. Member 76 has upstanding abutments 86 which abut the ends of ribs 78 so that, as member 76 is pulled rearwardly, it does not continue under inertia beyond a required index position or draw teeth 80 out of engagement with teeth 72.

Figure 10:
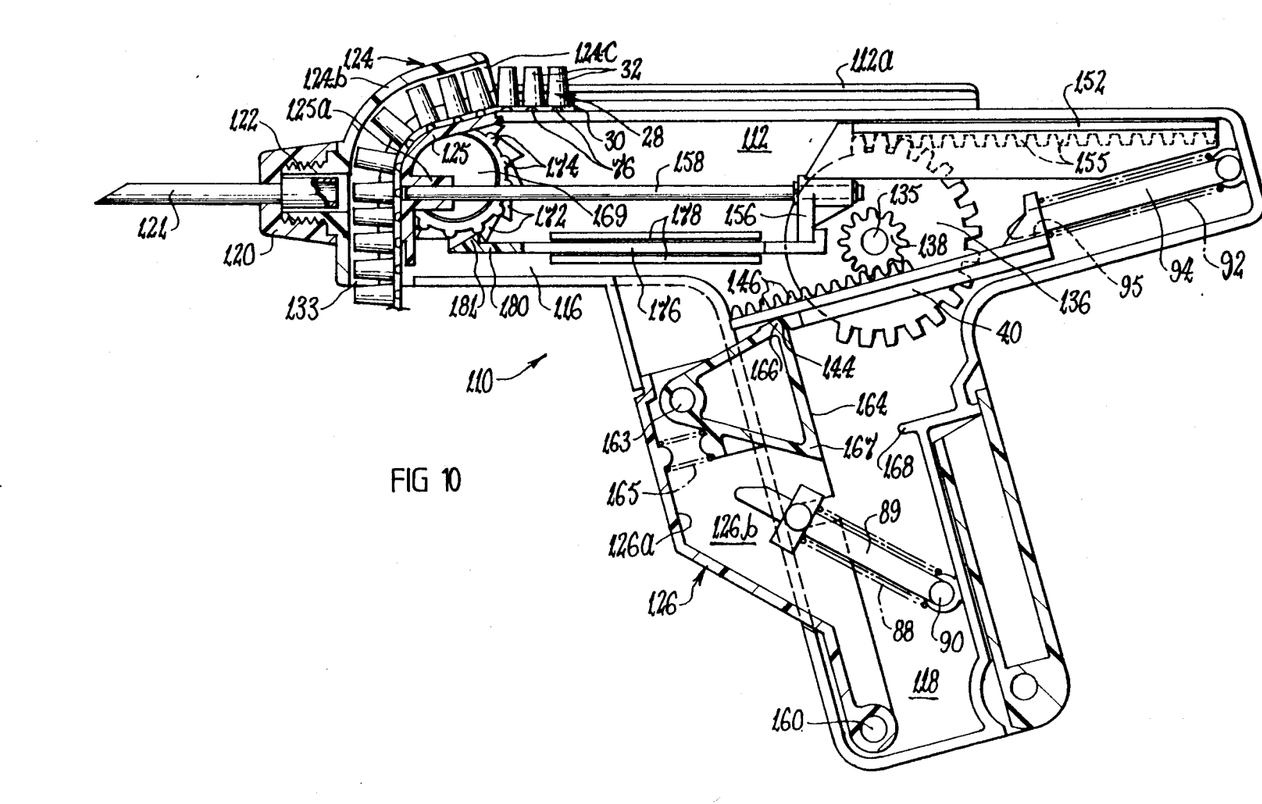
FIG. 10 shows detail similar to that of FIG. 5 but in respect of a first modified form of gun.

The gun 110 of FIG. 10 is similar to that of FIG. 1 in overall form and general operation and corresponding parts have the same reference numeral, plus 100. However, return of trigger 126 to its rest position is by means of a spring 88 acting on a lever arm 89 which is pivotable on pin 90 so as to move with trigger 126. Also, instead of a spring acting directly on member 152, a compression spring 92 acts directly on member 140. Spring 92 extends around rod 94 which passes through an aperture 95 in upstanding tab 96 of member 140 and guides the latter. Also, teeth on member 140 mesh directly with gear 138. Additionally, member 162 is of a triangular outline, and is urged towards member 140 by springs 165 acting between member 162 and web 126b of trigger 126. Despite these differences, the overall operation is as described with reference to the gun of FIG. 1

Figure 11:
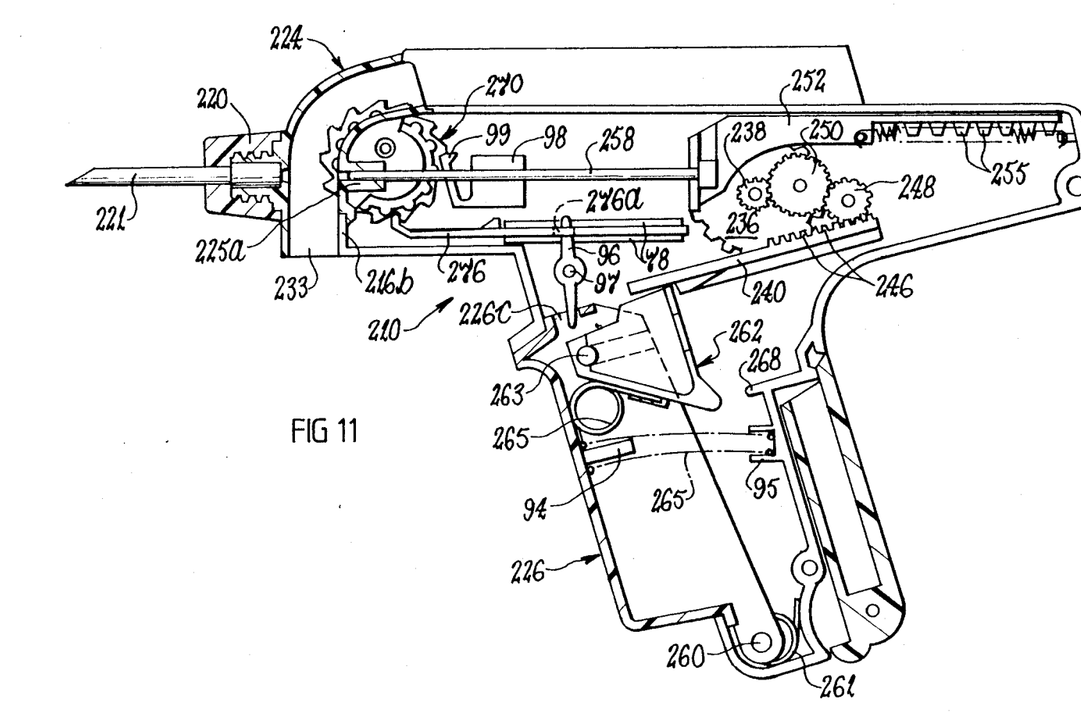
FIG. 11 shows detail similar to that of FIG. 5 but in respect of a second modified form of gun.

The gun 210 of FIG. 11 is similar in overall form and general operation to that of FIGS. 1 to 9, and corresponding parts are identified by the same reference numerals plus 200. However, in this instance, spring 265 is in the form of a helical compression spring having one end received on pin 94 of web 226a of trigger 226 and its other end located in locating boss 95 on the rear wall of handle 218. Also, advance and retraction of member 276 is not achieved by means of finger 256, but by means of a toggle 96 actuated by trigger 226. As shown, toggle 96 is centrally mounted on a pin 97 on one of casings 212,214 and has its lower end loosely received in opening 226c defined in the upper end of handle 226. The upper end of toggle 96 is loosely received in opening 276a in member 276. As trigger 226 is squeezed for a firing operation, against the bias of spring 265, toggle 96 pivots on pin 97, with its lower end being drawn rearwardly and its upper end moving forwardly to advance member 276; with reversal of that pivoting and retraction of member 276 occurring on release of trigger 226 on completion of a firing operation. During such movement of member 276, the tooth 281 of each of its fingers 280 locate behind a next tooth 272 of the respective wheel 270, to index wheels 270 and advance the pellet cartridge as previously described.

On each of casings 212,214, there is a respective block member 98 having a resilient detent finger 99. Each finger 99 rides against teeth 272 of a respective index wheel 270, and ensures accurate indexing of wheels 270 under the action of trigger 226, toggle 96 and member 276. Such detent arrangement can, if required, be used in the gun of FIGS. 1 to 96 or in that of FIG. 10.

The gun 310 of FIGS. 21 to 25 readily will be understood from the foregoing. The overall arrangement is similar to that of FIGS. 1 to 9, and corresponding parts have the same reference numeral, plus 300.

Figure 23:
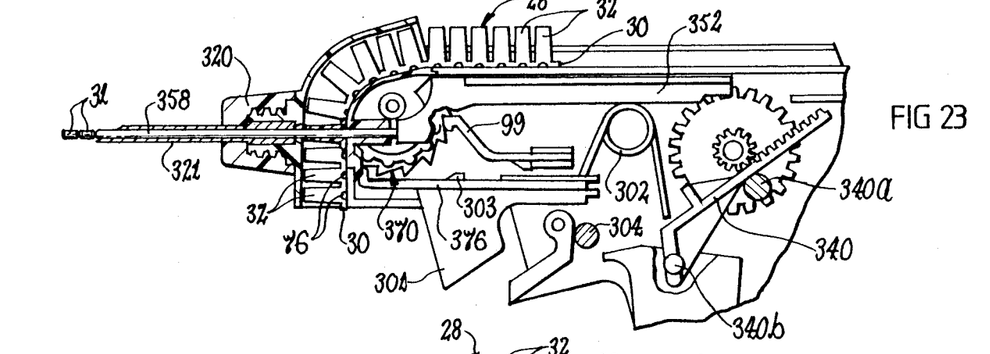
Figure 24:
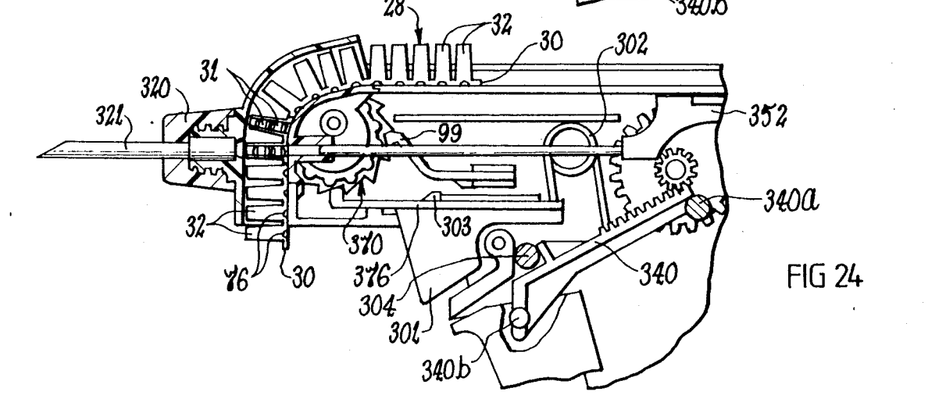
Figure 25:
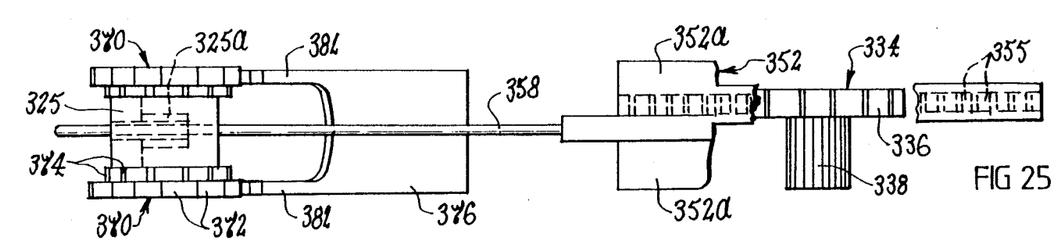
FIG. 25 shows details of the gun of FIG. 21.

As in the previous embodiments, gun 310 is intended for use with a flexible cartridge 28 of pellets, such as shown in FIG. 14. In FIG. 23, a cartridge 28 is shown with the gun in the process of discharging two pellets 31 from a holder 32 in a fourth of successive firing operations. FIG. 24 shows cartridge 28 after it has been indexed by one position along guide 324, to present the next holder 32 in line for discharge of its pellets 31 in a fifth firing operation.

As previously described, discharge of pellets 31 is effected by means of an elongated pin or needle 358 the free end of which passes through guide sleeve 325a of guide 324 located at the forward end of barrel 316. The other end of the needle 358 is mounted on a carrier member 352 which is in the form of a rack with teeth 355 on its underside. The carrier 352 has laterally projecting guides 325a (see FIG. 25) which are received within ribs 354 formed in the casing parts 312,314 so that carrier 352 is constrained for linear movement. Teeth 355 engage a pinion 336 of member 334 mounted for rotating on a pin 335.

The pinion 336 is formed integrally with a small diameter pinion 338 which meshes with a rack 340 and is held in engagement therewith by a rack guide post 340a of one of casings 312,314. The forward end of the rack 340 is connected by means of a pin 340b to trigger 326. The trigger 326 is elongate and projects from an elongate opening formed in the forward side of the handle 318. The lower end of the trigger 318 is pivoted to the handle at pin 360 and a return spring 361 biases the trigger 326 to a forward position, as shown in FIG. 21.

In use of the device 310, the user can retract the trigger 326 by a squeezing action of the fingers. This causes the rack 340 to rotate the pinions 338 and 336. The carrier 352 will therefore be moved in the forward direction with a linear velocity which is faster than the inward velocity of the trigger 326, owing to the gearing up provided by the pinions 338 and 336. The needle 358 will therefore be quickly advanced and will engage the pellet or pellets 31 an carry them through the hollow needle 321 and then beyond the end of the needle 321 for implanting in an animal.

Figure 21:
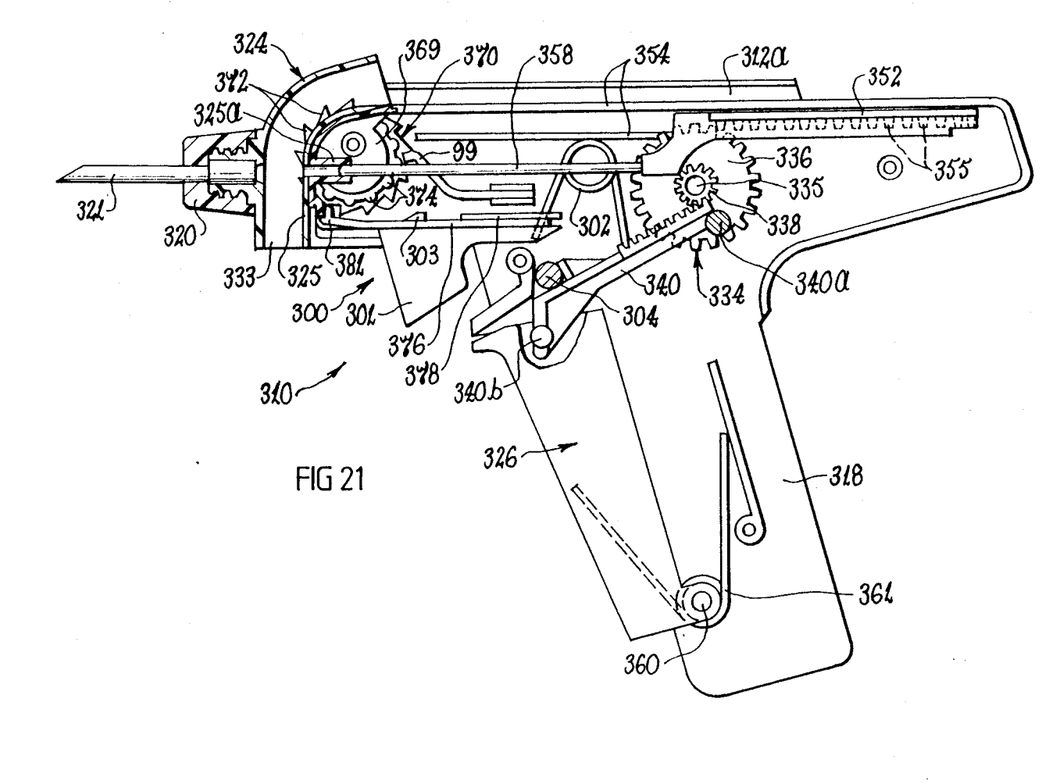
FIG. 21 shows detail similar to that of FIG. 5 but in respect of a third modified form of gun.

When the trigger 326 is released, the spring 361 will cause the trigger to return to its position shown in FIG. 21 whereby the needle 358 is retracted. When the needle 358 is in its retracted position, the cartridge 28 can be advanced by a pellet advance mechanism 300 which is actuated by a supplementary, pellet advance trigger 301 separate from trigger 326.

Figure 22:
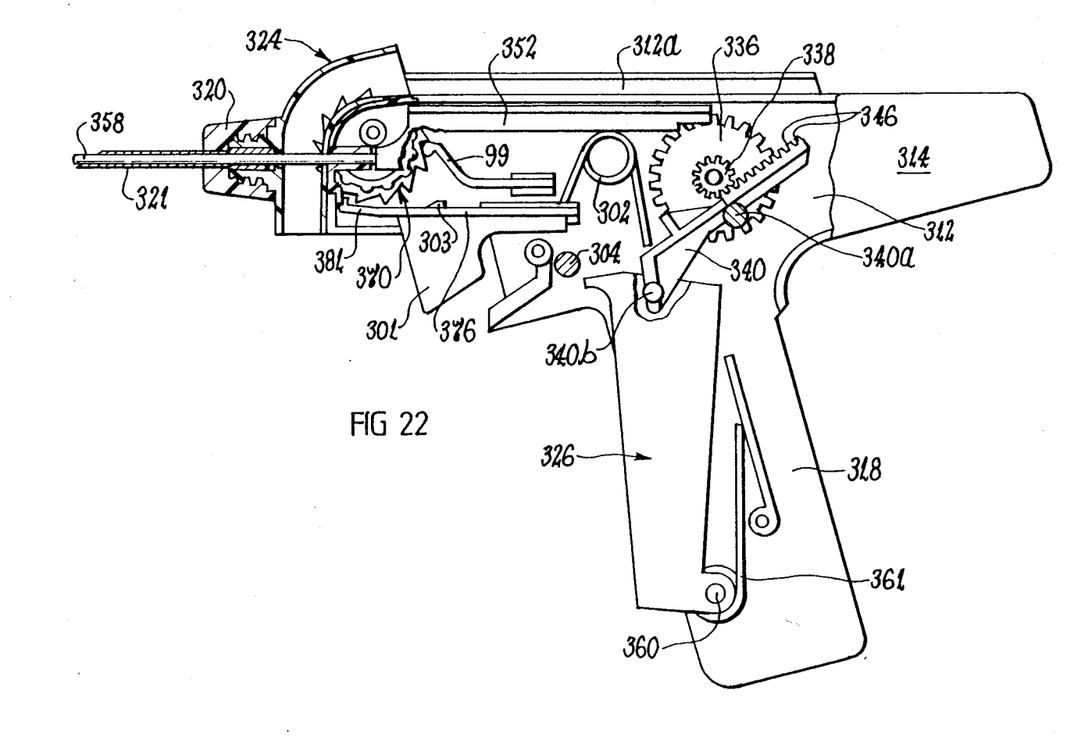
FIGS. 22 to 24 show the gun of FIG. 21 in the course of respective stages of actuation.

The pellet advance machanism 300 includes a hub member 369 which is held stationary between the casing parts 312,314. It includes a central guide surface 325 which supports the base strip 30 of the cartridge, the sleeve 325a thereof being formed integrally with the hub portion 369. The hub portion 369 forms a support of a pair of drive wheels 370 which include projections 374. The projections 374 mesh with the fingers 376 projecting laterally from the sides of the strip 30. The arrangement is such that when the wheels 374 are rotated, the projections 374 cause the cartridge 28 to be moved in unison therewith. The wheels 370 are formed integrally with drive gear teeth 372 engagable by a pair of drive lugs 381 located at the forward end of a slide plate 376 which is mounted for sliding movement between the casing parts 312,314. The slide plate 376 is connected to the supplementary trigger 301. A spring 302 biases the plate 376 and trigger 301 towards the forward position, as illustrated in FIGS. 21 and 22.

When it is desired to advance the cartridge 28, the user pulls the trigger 301 and this causes the lugs 376 to engage the drive gear theeth 372, thereby causing rotation thereof and hence of the drive wheels 370. This causes movement of the cartridge 28 through the feed guide 24. The stroke of the plate 376 is limited by means of a stop 303, the arrangement being such that the cartridge 28 is advanced by exactly the distance between the holders 32 thereof in which the pellets are located. A detent ratchet 99 which is engagable with the teeth 372 of the wheels 370 ensure that the latter do not rotate in the reverse direction when the plate 376 returns to its position under the influence of the spring 302. This ensures that the cartridge 28 will be in its correct position in readiness for ejection of pellets 31 caused by actuation of the trigger 326.

The described device is inherently less noisy than conventional devices because the function of expelling pellets and advancing pellets in readiness for expelling are separately manually effected. Particularly, no reliance is placed on recoil action to achieve operation.

Furthermore, in the illustrated embodiment, a rubber cushion 304 is provided so as to cushion movement of the rack 340 under the influence of the return spring 361. A similar cushion arrangement could be provided to cushion movement of the slide plate 376. The cushion 304 further makes the device quieter in operation and hence less disturbing to the livestock upon which the device is used.

In use of the device, the operator operates the trigger 301 so as to position pellets 31 in readiness for ejection. The needle 321 is then introduced into the livestock at a selected location and then the trigger 326 is pressed causing expulsion of the pellets 31 into the animal. The trigger 326 is then released and the needle 321 withdrawn from the animal.

Figure 26:
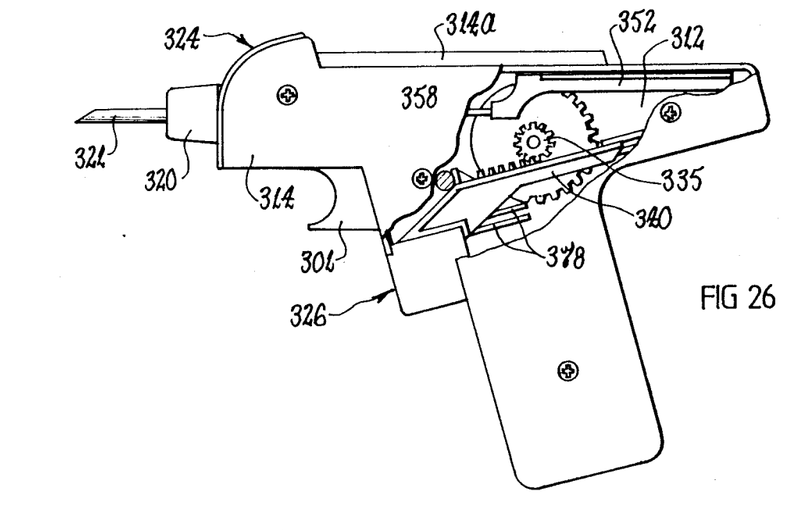
FIG. 26 shows a variant of the gun of FIGS. 1 to 9, or that of any one of FIGS. 11, 12 and 22 to 25.

Many modifications will be apparent to those skilled in the art. For instance, FIG. 26 illustrates an alternative arrangement in which the trigger 326 is mounted for sliding movement in the handle 318 rather than pivoting movement as shown in the previous embodiments. In this arrangement, the rack 340 can be formed integrally with the trigger 326 and arranged to slide in guideway 342 formed in the casing parts 312,314. Many further modifications will be apparent to those skilled in the art.

Finally, it is to be understood that various alterations, modifications and/or additions may be introduced into the constructions and arrangements of parts previously described without departing from the spirit or ambit of the invention.

We claim:

1. An implant gun for implanting an insert or pellet into or below tissue of an animal, the gun comprising a body, said body comprising a barrel, said barrel having a hand grip extending therefrom; a trigger mounted on said hand grip for successive manual firing operations; at least a portion of said barrel defining a guideway along which a series of pellets or implants are movable, said guideway comprising an outlet to define a discharge position through which said pellets or implants can be discharged from the gun, said gideway extending forwardly along said barrel and having a terminal portion of arcuate form which curves across the outlet of said barrel; the body also housing a discharge mechanism and an advance mechanism, said discharge mechanism being operable by manual operation of said trigger when in a firing position, whereby a pellet or implant present to said discharge position can be discharged from the gun; and said advance mechanism being operable to index the series of pellets or implants along said guideway.

2. A gun according to claim 1, in which is located a slide member which can slide between a retracted position and an advanced position on operation of the trigger, said slide member being connected to an ejection pin whereby movement of the slide member between its retracted position and its advanced position causes the pin to move between its retracted and advanced positions.

3. A gun according to claim 2, wherein the discharge mechanism includes an elongate ejection pin which extends longitudinally within the barrel, the ejection pin being longitudinally movable such that, during each firing operation, the pin is moved from a retracted position in which a forward end thereof is located rearwardly with respect to an outlet of the barrel, to an advanced position in which the forward end of the pin projects through the outlet sufficiently to eject a pellet previously presented to the discharge position.

4. A gun according to claim 3, wherein on completion of a firing operation, the ejection pin is returned to its retracted position under the action of resilient biasing means, with the ejection pin being movable to its advanced position against the action of the biasing means.

5. A gun according to claim 3, wherein the discharge position for successive pellets is located closely adjacent and in line with the forward end of the ejection pin and the outlet of the barrel.

6. A gun according to claim 2, wherein the slide member is movable along a track, channel or guide way defined within the barrel by longitudinal ribs formed on the inner surface of opposed sides of the barrel.

7. A gun according to claim 2, wherein the slide member is in the form of a toothed bar member movable linearly within the barrel under the action of a gear wheel engaged therewith and mounted within the barrel for rotation on a fixed axis, the gear wheel being rotated by drive from the trigger, as the trigger is squeezed.

8. A gun according to claim 7, wherein the gear wheel is rotatable in a first direction, in which it moves the slide member and the ejection pin to their advanced positions, under the action of the trigger, upon the latter being squeezed from a rest position for a firing operation.

9. A gun according to claim 8, wherein the trigger is urged to its rest position by a return spring, with the return spring providing a resilient force against which the trigger is squeezed in a firing operation.

10. A gun according to claim 8, wherein drive is provided by the end of the trigger adjacent the barrel.

11. A gun according to claim 10, wherein the trigger, engages and drives the gear wheel by at least one secondary gear in driving engagement with the gear wheel, with a drive ratio chosen which results in movement of the slide member, from its retracted to its advanced position, which exceeds the distance moved by the trigger in a firing operation.

12. A gun according to claim 8, wherein drive is provided by an actuating member movable with the trigger as the latter is squeezed, by means of a series of teeth engaged with the gear wheel.

13. A gun according to claim 12, wherein said actuating member moveably engages and drives the gear wheel by at least one secondary gear in driving engagement with the gear wheel, with a drive ratio chosen which results in movement of the slide member, from its retracted to its advanced position, which exceeds the distance moved by the trigger in a firing operation.

14. A gun according to claim 12, wherein the series of teeth is on an actuating member which engages the gear wheel on the side thereof diametrically opposed to that side engaged by the slide member; the actuating member being movable rearwardly with respect to the barrel to rotate the gear wheel in the first direction and causing forward movement of the slide member.

15. A gun according to claim 14, wherein the drive from the trigger to the gear wheel is operational only during squeezing of the trigger, and is disengaged when the trigger is squeezed substantially to complete a firing operation to enable reversal of the direction of rotation of the gear wheel under the action of biasing means acting on the slide member and independent return of the trigger to its rest position.

16. A gun according to claim 14, wherein the actuating member is a straight toothed bar movable endwise along a track, channel or guideway defined within the body of the gun adjacent the junction of the barrel and hand grip.

17. A gun according to claim 16, wherein the actuating member has an abutment face or shoulder at which a force is applied on squeezing the trigger, with the force acting to move the actuating member, with the trigger having a portion which abuts the face or shoulder such that, on squeezing the trigger, the actuating member is pushed along such track, channel or guideway and that portion is moved clear of the face or shoulder when the trigger is substantially fully squeezed to complete a firing operation.

18. A gun according to claim 17, wherein engagement between the trigger and the face or shoulder is by means of a catch member pivotally mounted on the trigger; with the catch member being constrained, by pivoting in one direction relative to the trigger, to remain in contact with the face or shoulder until the trigger has been substantially fully squeezed.

19. A gun according to claim 18, wherein the catch member is resiliently urged in the one direction by biasing means, with a guide or camming member causing pivoting of the catch member in the reverse direction, out of contact with the face or shoulder, when the trigger has been substantially fully squeezed.

20. A gun according to claim 2, wherein the advance mechanism is positioned so as to engage the series of pellets, and is operable to advance the series, substantially on completion of a firing operation to eject at least one pellet, so as to position at least one next pellet of the series at the discharge position.

21. A gun according to claim 20, wherein the advance mechanism includes at least one index wheel which engages the series of pellets, the index wheel being rotatable for advancing the series in a step-wise fashion through a small arc substantially on completion of each firing operation.

22. A gun according to claim 21, wherein the guideway for the series of pellets has a portion of arcuate form, and the at least one index wheel is rotatable on an axis within the arc, such as substantially co-incident with the centre of curvature of that portion.

23. A gun according to claim 21, wherein the at least one index wheel is rotatable on a hub member mounted within the barrel, a transverse opening being provided in the hub with the ejection pin extending through the opening at least when in its advanced position.

24. A gun according to claim 20, wherein the at least one index wheel is rotatably indexable by an indexing member adjustably engaged with the at least one index wheel and reversably movable for advancing the latter.

25. A gun according to claim 20, wherein the advance mechanism is actuated in response to actuation of the discharge mechanism, substantially on completion of a firing operation.

26. A gun according to claim 25, wherein the advance mechanism has an indexing member advanced and retracted by a coupling member provided between the trigger and the indexing member, such that as the trigger is squeezed in a firing operation, it advances the slide member, while it also retracts the slide member as it returns to its rest position.

27. A gun according to claim 26, wherein the coupling member comprises a lever or toggle pivotally mounted intermediate its ends within the gun body and having respective ends coupled to the trigger and the indexing member such that, as the trigger is squeezed during a firing operation, the end of the level or toggle coupled to the trigger is drawn therewith and the lever or toggle is pivoted so as to move its other end in the opposite direction and thereby advance the indexing member, return of the trigger to its rest position causing reversal of the pivoting of the lever or toggle and thereby retracts the indexing member.

* * * * *

UNITED STATES PATENT AND TRADEMARK OFFICE
CERTIFICATE OF CORRECTION

PATENT NO.  : 4,976,686
DATED       : December 11, 1990
INVENTOR(S) : Keith V. Ball; Karl-Heinz Halblander; Barry N. Loftus It is certified that error appears in the above-identified patent and that said Letters Patent is hereby corrected as shown below:

In Column 1, line 28, delete "a", and insert therefor --of--.

In Column 3, line 44, delete "pivioting" and insert therefor --pivoting--.

In Column 6, line 40, delete "26" and insert therefor --25--.

In Column 7, line 25, delete "24" and insert therefor --14--.

In Column 10, line 3, delete "96" and insert therefor --9--.

In Column 11, line 10, delete "theeth" and insert therefor --teeth--.

In Column 1 (Column 11, line 68), delete "gideway" and insert therefor
    --guideway--.

In Column 1 (Column 12, line 7), delete "present" and insert therefor
    --presented--.

Signed and Sealed this

Eighth Day of September, 1992

Attest:

DOUGLAS B. COMER

*Attesting Officer*　　*Acting Commissioner of Patents and Trademarks*